United States Patent [19]
Pang et al.

[11] Patent Number: 5,643,577
[45] Date of Patent: Jul. 1, 1997

[54] ORAL VACCINE COMPRISING ANTIGEN SURFACE-ASSOCIATED WITH RED BLOOD CELLS

[75] Inventors: Gerald Toh Pang; Robert Llewellyn Clancy, both of Newlambton, Australia

[73] Assignee: The University of Newcastle Research Associates Limited, Australia

[21] Appl. No.: 940,899

[22] PCT Filed: Apr. 24, 1991

[86] PCT No.: PCT/AU91/00159

§ 371 Date: Oct. 23, 1992

§ 102(e) Date: Oct. 23, 1992

[87] PCT Pub. No.: WO91/16073

PCT Pub. Date: Oct. 31, 1991

[30] Foreign Application Priority Data

Apr. 24, 1990 [AU] Australia ............... PJ9783/90

[51] Int. Cl.[6] ............ A61K 39/145; A61K 39/12; A61K 39/385
[52] U.S. Cl. ............... 424/206.1; 424/196.11; 424/194.1; 424/193.1; 424/204.1
[58] Field of Search ............... 424/88, 89, 90, 424/93 R, 93 B, 93 C, 93 U, 93 AA, 184.1, 193.1, 194.1, 196.11, 203.1, 206.1, 209.1

[56] References Cited

U.S. PATENT DOCUMENTS

| | | | |
|---|---|---|---|
| 4,157,390 | 6/1979 | Parry et al. | 424/92 |
| 4,403,037 | 9/1983 | Coates | 436/521 |
| 4,904,468 | 2/1990 | Gill et al. | 424/89 |
| 5,075,109 | 12/1991 | Tice et al. | 424/88 |

FOREIGN PATENT DOCUMENTS

| | | |
|---|---|---|
| 649435 | 2/1979 | U.S.S.R. |
| 1563839 | 4/1980 | United Kingdom |
| 1580539 | 12/1980 | United Kingdom |

OTHER PUBLICATIONS

Farag–Mahmod et al (1988) Immunogenicity and efficacy of Orally–Vaccine 6:262–268.
White et al (1986) Medical Virology. Academic Press, NY, pp. 509–512.
Posnett et al (1988) "A Novel Method . . . " J. Biol. Chem 263:1719–1725.
Dawn et al (1986) "Method for generating . . . " Met. Enzemol. 121:42–51.
Waugh et al (1976) "Visco elastic properties . . ." Microvasc Res 12 (3):291–304, Abstract Only.
Milich et al (1988) PNAS 85(5) 1610–4. Abstract only.
Webster's New Ninth Collegiate Dictionary, 1990, p. 70.
Mullhache et al. (1988) *Immunol. Cell Biol.*, 66:153–157.
Pang et al. "A Novel Particulate Influenza Vaccine Induces Long–Term and Broad–Based Immunity in Mice after Oral Immunization," *Journal of Virology* (Feb. 1992) 1162–1170.
Derwent Abstract Accession No. 83738/46, Class B04, SU,A 649435 (UFA Vaccine Sera) Feb. 28, 1979.
Derwent Abstract Accession No. 55028A/30, Class J04, SU,A 562064 (Sverd Virus Infect) Oct. 10, 1977.
Derwent Abstract Accession No. 85–089709/15, Class J04, JP,A 60–038656 (Green Cross Corp.) Feb. 28, 1985.
Jones, et al. "Cellular Immune Responses in the Murine Lung to Local Immunization with Influenza A Virus Glycoproteins in Micelles and Immunostimulatory Complexes (Iscoms)" *Scand. J. Immunol.* 27, 645–652, 1988.
Kreuter et al. "Long–Term Studies of Microencapsulated and Adsorbed Influenza Vaccine Nanoparticles" *J. Pharm. Sci.* 70, No. 4, 367–371, Apr. 1981.

*Primary Examiner*—Lynette F. Smith
*Attorney, Agent, or Firm*—Scully, Scott, Murphy & Presser

[57] ABSTRACT

Red blood cells or derivatives thereof such as ghost preparations can act as a potent carrier for orally administered antigens. Mucosal immunity in particular can be effectively induced against such viruses as influenza when adsorbed to chicken red blood cells and orally administered.

13 Claims, 8 Drawing Sheets

ORAL VACCINE COMPRISING ANTIGEN SURFACE-ASSOCIATED WITH RED BLOOD CELLS

This invention relates generally to vaccines and in particular, although not limited to, influenza vaccines appropriate for oral administration.

Currently, most vaccines are administered parenterally with consequent problems arising from the invasive nature of the administration route. For instance, it has been proposed, in U.S. Pat. No. 4,157,390 to use red blood cells as vehicles for the presentation of enteropathogenic antigens in a parenteral vaccine administered to prepartum sows. A further disadvantage of parenteral administration is that, in general, it induces a better blood borne immune response than a mucosal one, yet the prophylaxis or treatment of some infective agents is more appropriately dealt with by a strong mucosal immunity. The parenteral nature of prior art vaccines has not in general resulted in a strong mucosal response.

To redress some of these problems, orally administered vaccines have been proposed against various infective agents. Unfortunately as the alimentary tract provides a hostile environment, it is only fortuitously, such as in the Sabin vaccine, that these have been effective.

It is an object of the present invention to provide a vaccine which redresses some of the disadvantages experienced in the past.

It has now been found that red blood cells and their derivatives can provide a potent orally administered vehicle for the presentation of antigens to the mucosal immune system. Therefore in accordance with a first aspect of the invention there is provided an oral vaccine comprising antigen surface-associated with red blood cells or derivatives thereof.

A second aspect of the invention provides a method of eliciting an immunoresponse, particularly a mucosal immune response, in a mammal the method comprising the oral administration of a vaccine as defined immediately above.

In general, the antigen will derive from an infectious agent. Such an infectious agent may be a virus, in particular those viruses in which a mucosal immunoresponse appears important in prophylaxis or acute infection. Examples of these include respiratory viruses such as influenza or rhinovirus, polio and certain gastrointestinal infections such as rotavirus. Other infections of mucosal like tissue include E. coli infections of the urinary tract and chlamydia infection of the eye in trachoma. The present invention can also invoke a systemic immunity suggesting uses in systemic infections such as hepatitis or tetanus. Other immunizing applications such as those intended for anti-allergy or contraceptive treatment may also be appropriate. The antigen may comprise a plurality of antigens to produce a multivalent vaccine for all strains of, for instance, influenza, present in a season. Alternatively or additionally, the antigen may comprise a plurality of antigens from different organisms thus leading to a single vaccine effective against more than one disease or condition.

The invention is not limited to the use of whole red blood cells in the vaccine, because derivatives thereof, such as ghosts or membrane preparations, can also yield the desired enhanced mucosal immunogenicity. One observation has been that the use of red blood cells provides extremely uniform size particles within the optimal 5 to 10 μm range optimally taken up by Peyers patches, see, for instance Jones et al. (1988) Scand. J. Immunol., 27, 645. Thus, by the use of the invention, an antigen can be effectively targeted to the Peyers patches, the "mucosal motor" for the activation of the common mucosal system. Previous attempts to target Peyers patches have failed due to difficulties in creating discrete uniform size particles, as shown by Kreuter et al. (1981) J. Pharmaceutical Sci., 70, 367.

An advantage of the orally administered red blood cell (or derivative) system of the present invention is that due to previous dietary exposure, the red blood cells are immunologically well tolerated by most individuals. It is therefore desirable that the red blood cells should originate from farm animals such as chickens, ducks, cows or sheep. Alternatively, to ensure hypoallergicity human red blood cells could be used.

The surface-association of the antigen with the red blood cell or derivative may take place through adsorption or binding via liganding or other chemical modification. One alternative is to bind the antigen to a lectin or antibody (fragment) having specificity for red blood cell markers. Preferably, however, the association takes place through the interaction of an indigenous (i.e. naturally present) receptor on the red blood cell, the receptor having specificity either for the antigen itself or for a linking or haptenic group attached to the antigen.

For instance, the influenza haemagglutinin glycoprotein (HA) binds avidly to a surface receptor of chicken red blood cells (CRBC). Influenza preparations, either live attenuated or inactivated, can be directly bound via the HA and surface receptor to the red blood cell (or derivative). Virus purification from culture supernates and vaccine preparation can be achieved in a single step by the simple addition of the red blood cell (or derivative) to the supernate. A preferred technique for preparing viral antigens utilizes gamma irradiation which appears to favourably maintain the antigenicity of the preparation.

The efficacy of antigen presentation on the red blood cell (or derivative) is such that very small amounts of antigen may induce an effective response, suggesting a potentiation or adjuvancy of this system. The small amounts of antigen required may allow the provision of the multivalent vaccines discussed above.

An unexpected feature of the present invention is that it has been shown to provide effective local and systemic stimulation, resulting in circulating and local antibodies which have a demonstrated prophylactic effect.

An embodiment of a vaccine in accordance with the invention will now be described by way of example only with reference to the following example and the accompanying FIGS. 1 to 11 which illustrate the results of the various experiments discussed in the Example. In particular FIG. 1 is a bar graph depicting the protection of mice to H3N2 viruses after oral vaccination with CRBC adsorbed with A/Qld/6/72 virus;

remove egg material and excess virus, virus-adsorbed CRBC were then resuspended in 2% sodium bicarbonate solution to $5 \times 10^8$ particles/ml.

For oral vaccination, Swiss male mice were administered 0.4 ml phosphate-buffered (unimmunised control) or 0.4 ml inactivated virus alone or CRBC (whole or lysed) absorbed with gamma irradiated virus (immunised) in sodium bicarbonate on each of days 1, 3 and 5. Ten days after the final dose the mice were challenged with live virus intranasally by inoculating 50 μl of live virus suspension in phosphate-buffered saline into each nostril using a micropipette. Four days after challenge, mice were killed. Virus and antibody titres in the lung homogenates were determined by MCDK virus infectivity assay and ELISA.

Figure 1:
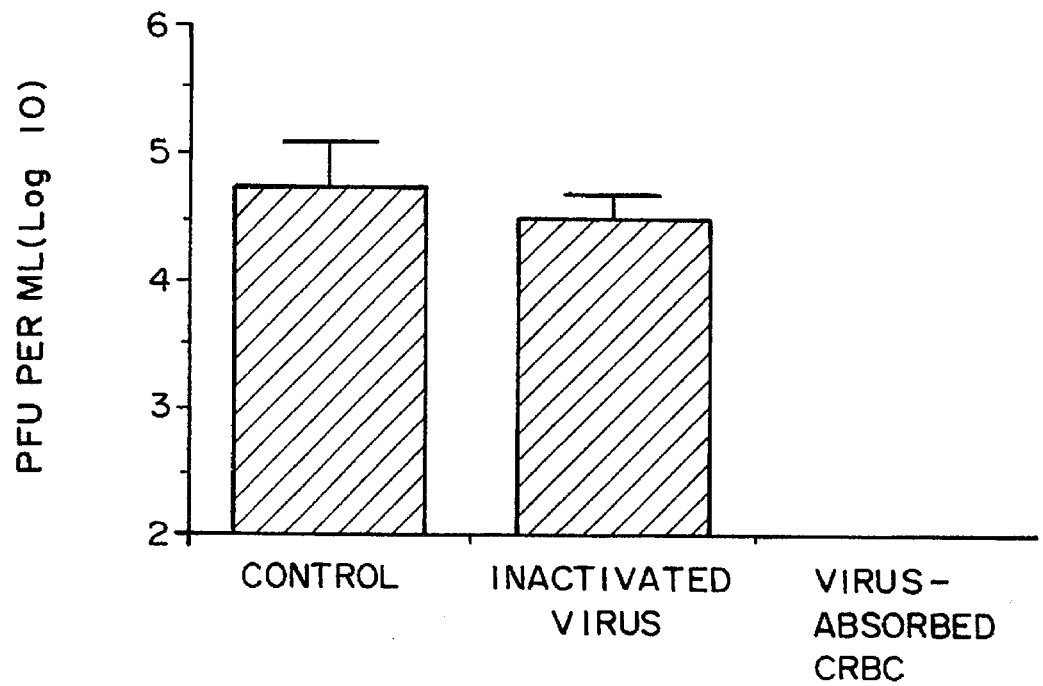
Figure 2:
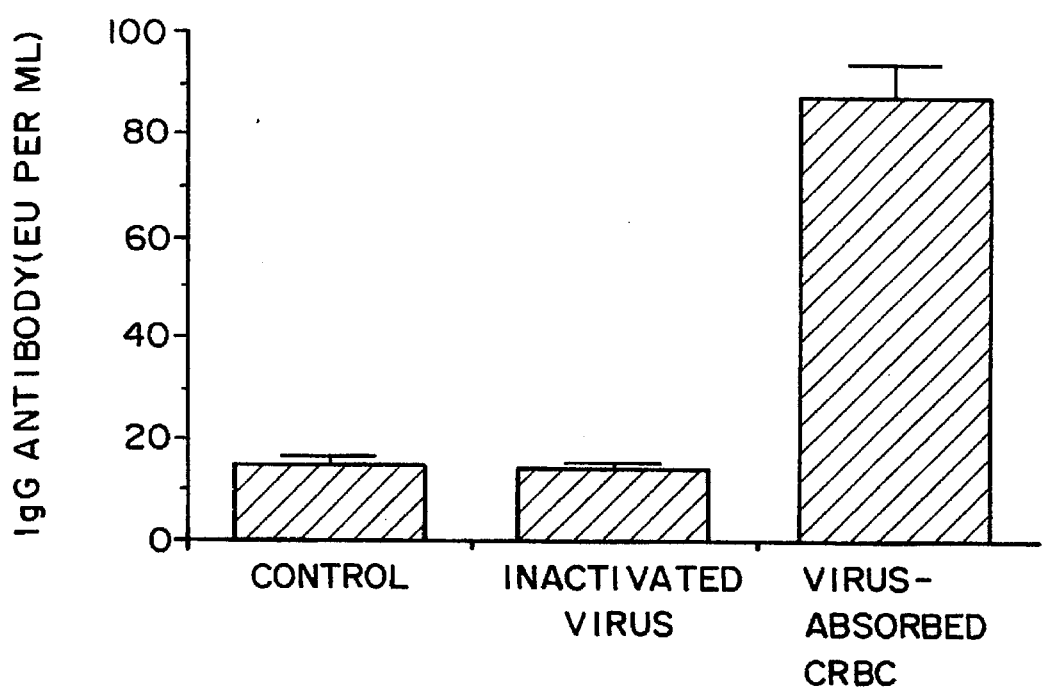
FIG. 2 is a bar graph depicting virus specific antibody titres of lung homogenates from mice after oral vaccination with virus adsorbed CRBC.

A representative experiment is shown in FIGS. 1 and 2. Mice immunized with PBS or inactivated virus were not protected against challenge with live virus in the respiratory tract compared to mice immunized with CRBC-adsorbed with gamma irradiated viruses. Further, there was a correlation between protection and the presence of virus-specific antibodies in respiratory secretion (FIG. 2). Protection and antibody response were dose-dependent, with mice being protected when immunized with CRBC adsorbed with virus as low as $\log_{10}$ 2 TCID as depicted in Table 1 which shows the antibody response and protection of mice from lung infection following oral vaccination with graded doses of A/Qld/6/72 virus adsorbed to CRBC.

TABLE 1

Antibody response and protection of mice from lung infection following oral immunization with CRC absorbed with graded doses of inactivated A/Qld/6/72 (H3N2) virus

| A/Qld/6/72 (H3N2) Immunization Dose | Lung | | Nasal Wash | |
|---|---|---|---|---|
| ($\log_{10}$ TCID$_{50}$) | IgG (EU/ml) | PFU/Lung | IgA (EU/ml) | PFU/ml |
| 0 | 4.8 ± 0.002 | 6.06 ± 0.08 | 5.6 ± 0.09 | 4.6 ± 0.15 |
| <1 | 17.2 ± 0.79 | 5.40 ± 0.24 | 10.1 ± 0.59 | 4.4 ± 0.23 |
| 2 | 67.5 ± 11.3 | 2.67 ± 0.84 | 51.6 ± 0.13 | <2 |
| 3 | 65.9 ± 8.5 | <2 | 42.9 ± 14.3 | <2 |
| 4 | 65.4 ± 8.4 | <2 | 14.9 ± 0.50 | <2 |

EXAMPLE

ORAL IMMUNISATION WITH INACTIVATED INFLUENZA VIRUSES USING CHICKEN RED CELL PARTICLES AS CARRIERS

Figure 3A:
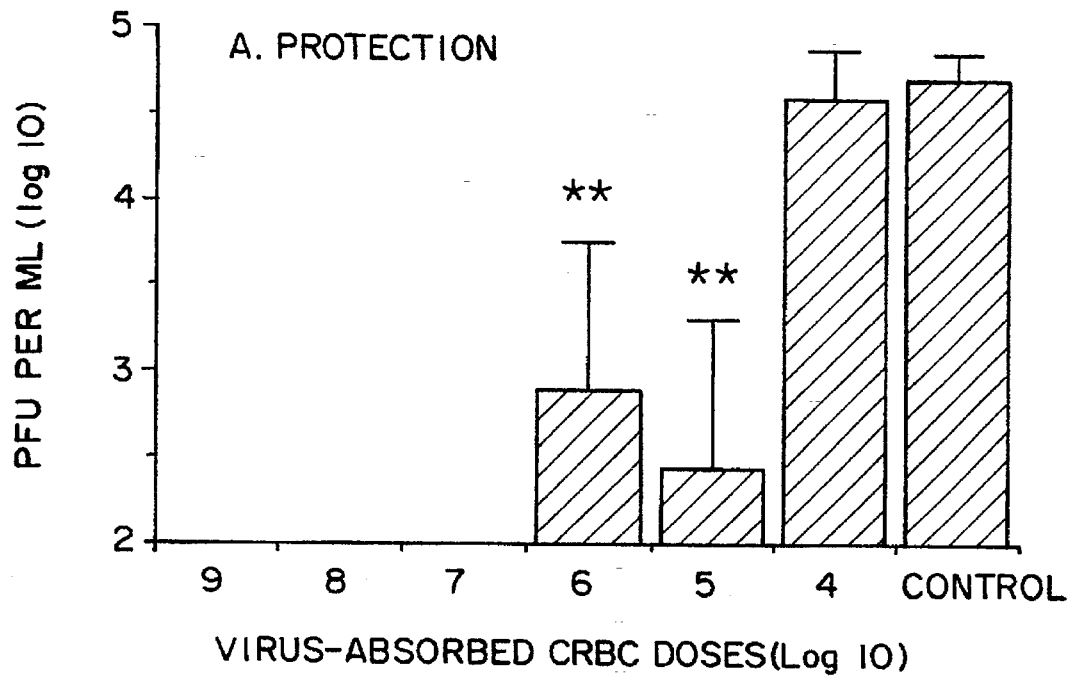
FIGS. 3A and 3B are bar graphs depicting lung antibody titre and protection of mice following oral vaccination with graded doses of CRBC adsorbed with A/Qld/6/72 virus.
Figure 3B:
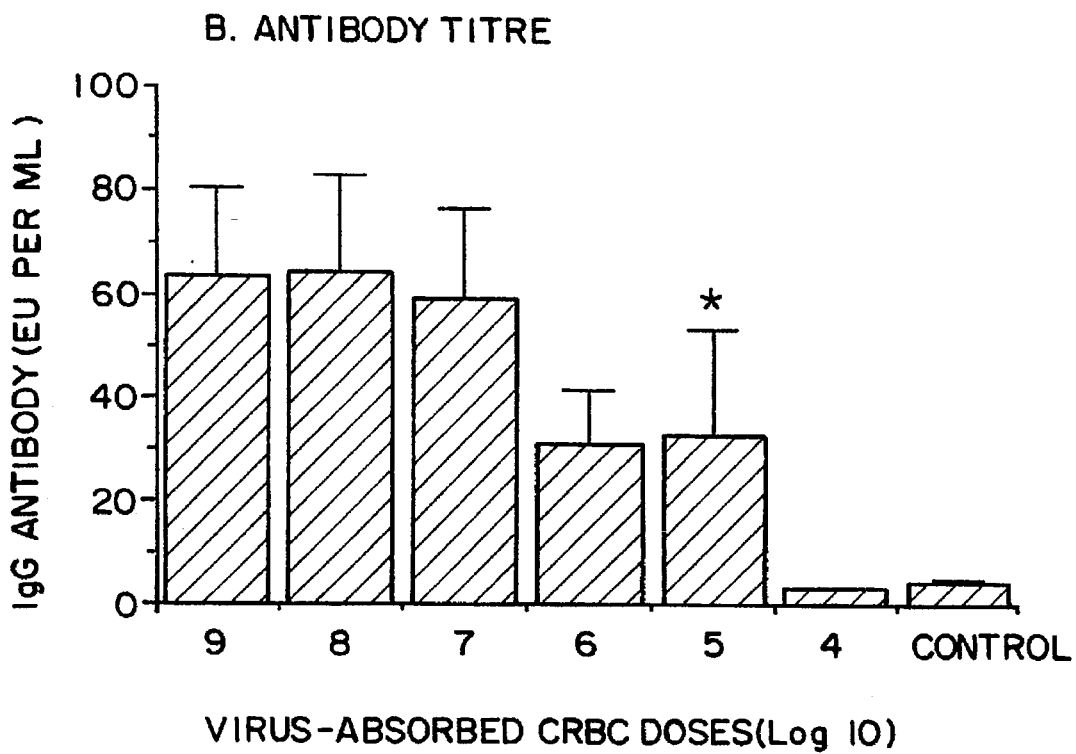
Figure 4A:
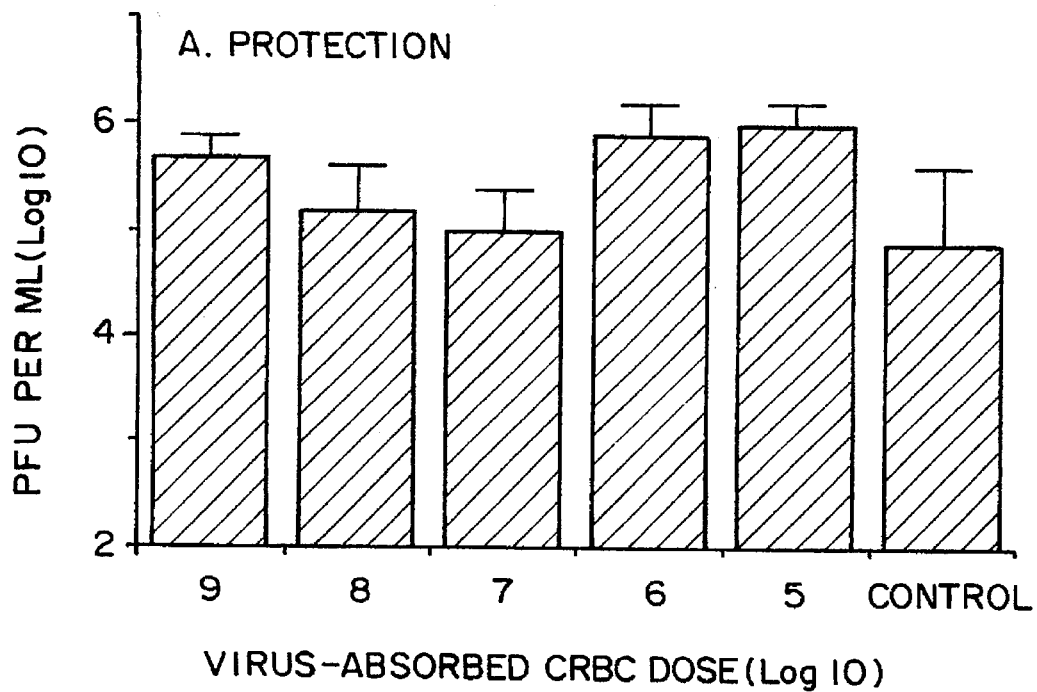
FIG. 4A and 4B are bar graphs depicting a similar experiment to FIG. 3 except the mice were immunised subcutaneously.
Figure 4B:
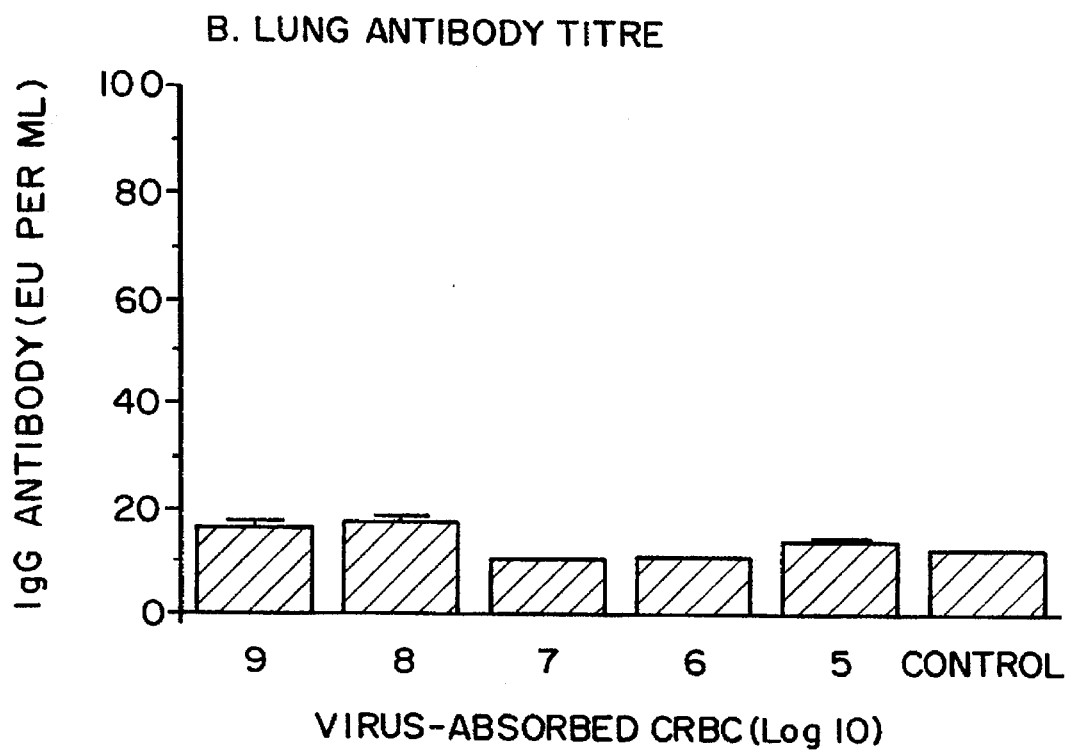
Figure 5:
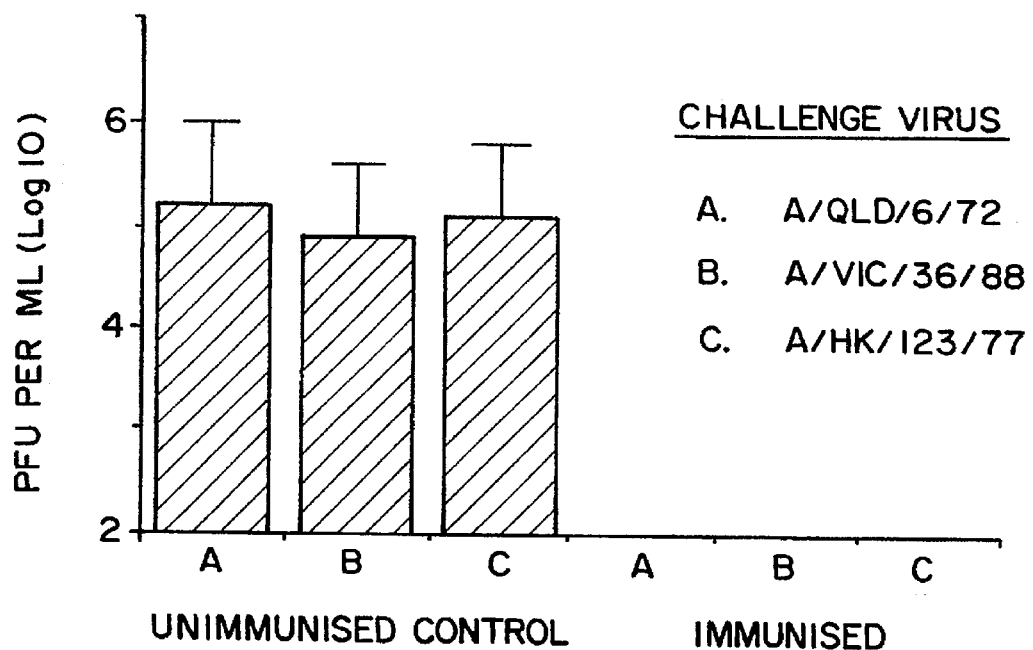
FIG. 5 is a bar graph depicting the protection of mice to A/Qld/6/72, A/Vic/36/88 and A/HK/123/77 viruses following oral immunisation with triple adsorbed virus.
Figure 6:
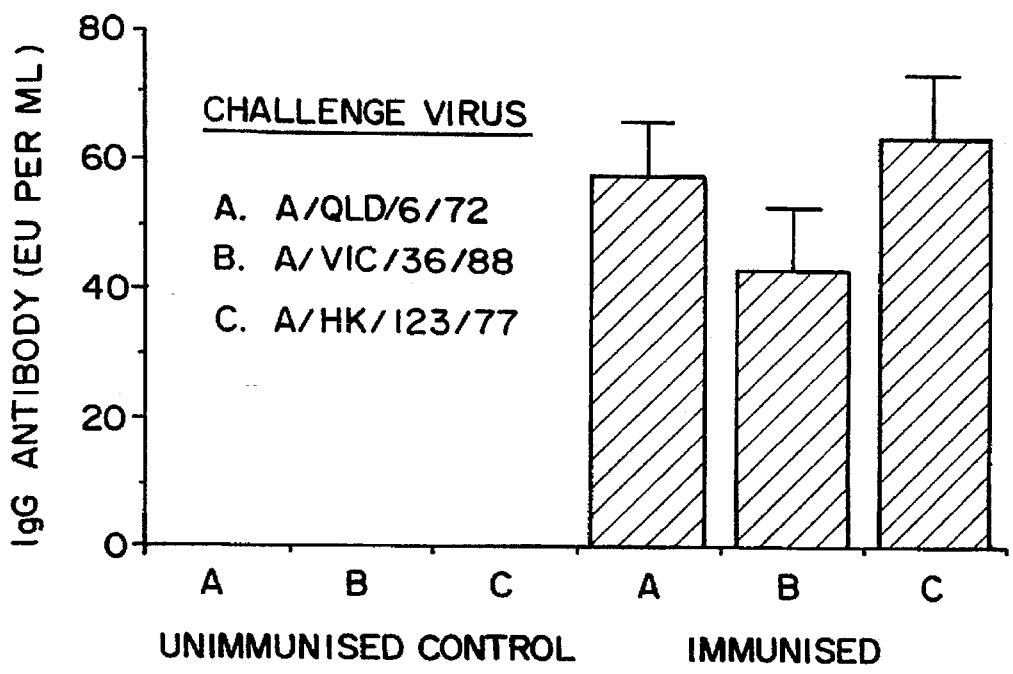
FIG. 6 is a bar graph depicting virus antibody specific for A/Qld/6/77, A/Vic/36/88 and A/HK/123/77 viruses following oral immunisation with triple adsorbed virus.

This Example is based on the ability of influenza virus, irrespective of antigenic drift, to bind to chicken red blood cell surface receptor through the haemagglutinin glycoprotein. Thus virus purification and vaccine preparation can be achieved in one single step. Briefly, chicken red blood cells were washed three times with phosphate-buffered saline (PBS) and hen resuspended to $10^{10}$ cells/ml in PBS. They were then used whole for virus adsorption or as 'ghosts' after lysis with Tris-buffered ammonium chloride solution. Adsorption was carried out at room temperature for 30 minutes with various dilutions of gamma irradiated ($2 \times 10^6$ rads, $^{60}$Co) allantoic fluid containing virus grown in specific-pathogen free eggs. After three washes with PBS to By comparing FIGS. 3 and 4 it can be seen that lung antibody titre following oral vaccination with the product of this invention is enhanced over that seen from subcutaneous administration. The versatility of the CRBC carrier system was demonstrated in an experiment in which triple absorbed virus CRBC was tested using A/Qld/6/72, A/Vic/36/88, and A/HK/123/77 viruses. All three viruses were cleared from the murine lung following challenge and the responses correlated with virus-specific antibody levels in respiratory secretion (FIGS. 5 and 6). Clearly, virus-absorbed CRBC particles are potent inducers of protective immunity in the respiratory tract when administered by the oral route. Table 2 on page 9 includes preliminary data from current studies, indicating cross protection following oral immunisation with absorbed virus.

TABLE 2

| Cross specific virus antibody* in respiratory secretion of mice following oral immunisation with A/6/Qld/2/72 (H3N2) influenza virus absorbed to CRBC | | | | | | |
|---|---|---|---|---|---|---|
| | A/Vic/36/88 (H1N1) | A/HK/123/77 (H1N1) | A/Qld/2/72 (H3N2) | *V(GT)007 (H6N1) (Recombinant) | *V(GT)-035/79 (H2N2) (Wild Variant) | *B/Vic/2/87 |
| Unimmunised | — | — | 4.6 ± 0.008 | — | — | |
| Immunised with A/Qld/6/72 (H3N2) absorbed CRBC | 68.4 ± 8.5 | 78.5 ± 9 | 123 ± 20 | 86.3 ± 9.0 | 95.4 ± 9.5 | 7.6 ± 0.7 |

*ELISA assay including whole virus

Figure 8:
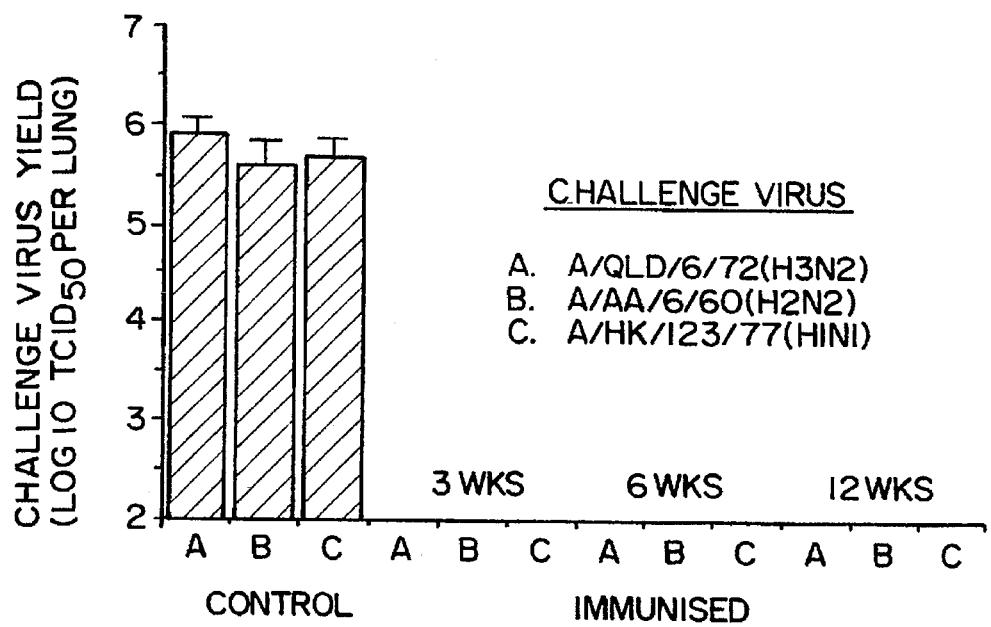
FIG. 8 is a bar graph depicting cross protection against heterotypic challenge in mice 3, 6 and 12 weeks after oral administration with A/Qld/6/72 (H3N3)

Heterotypic cross protection and the duration of protection were assessed by immunizing groups of mice with $4\times10^7$ A/Qld/6/72 (H3N2) virus absorbed CRBC and challenging each group with $Log_{10}$ 5.6 TCID A/Qld/6/72 (H3N2), A/AA/6/60ca (H1N1) and A/HK/123/77 (H2N2) respectively. Three weeks, 6 weeks and 12 weeks after oral immunisation, mice were challenged with live wild-type viruses from different sub types. As shown in FIG. 8 viruses were completely cleared from the lung. Virus clearance correlated with antibody against the homologous strain as well as cross protective antibody against the heterologous strains. Similar results were observed in the nasal wash in terms of virus clearance and antibody levels. The results were validated using the HI test to determine antibody levels in lung homogenates and nasal washes, which correlate with protection.

Figure 10A:
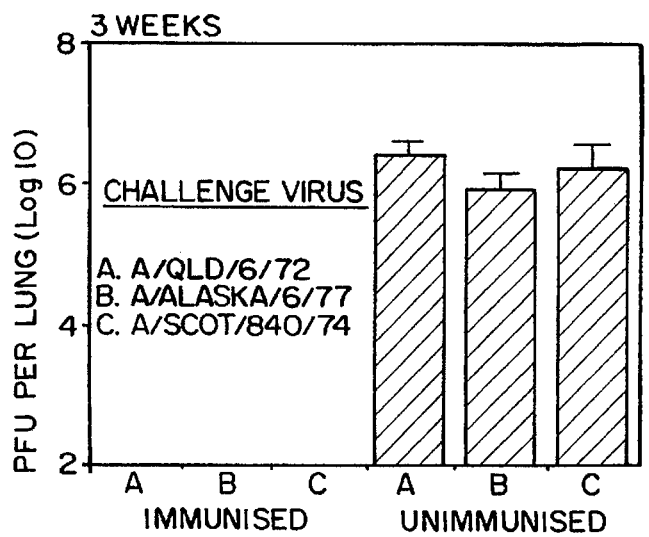
FIG. 10 is a bar graph depicting homotypic cross protection induced by A/Qld/6/72 (H3N2) to differing viruses within the H3N2 subtype.
Figure 10B:
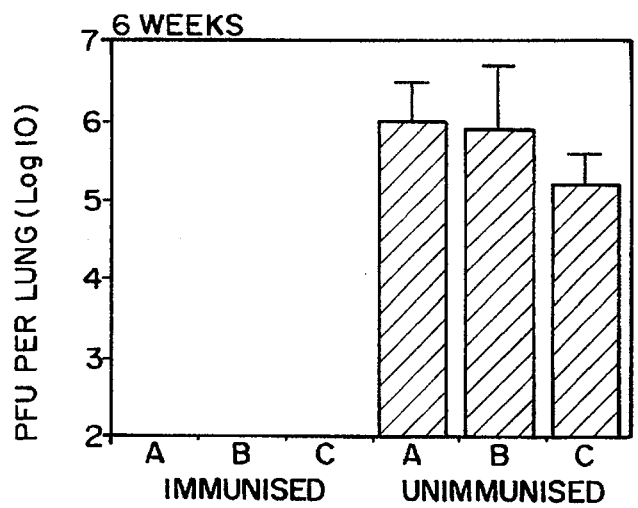
Figure 10C:
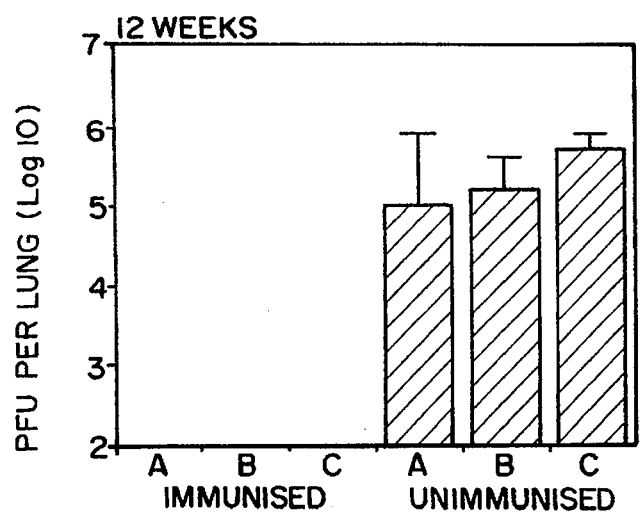
Figure 11A:
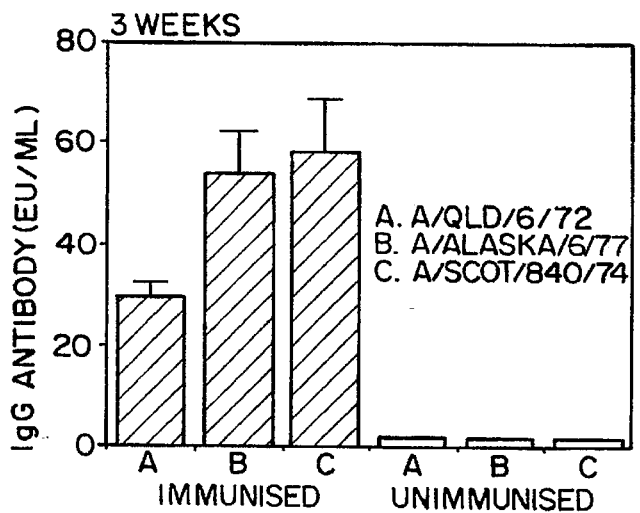
FIG. 11 is a bar graph depicting correlation between antibody titre and homotypic cross protection over time.
Figure 11B:
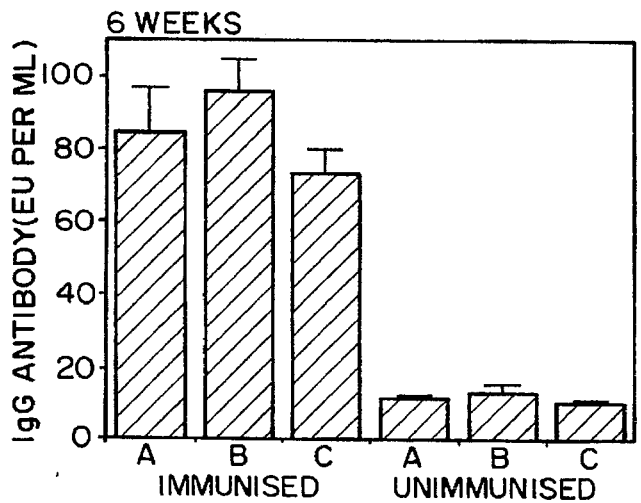
Figure 11C:
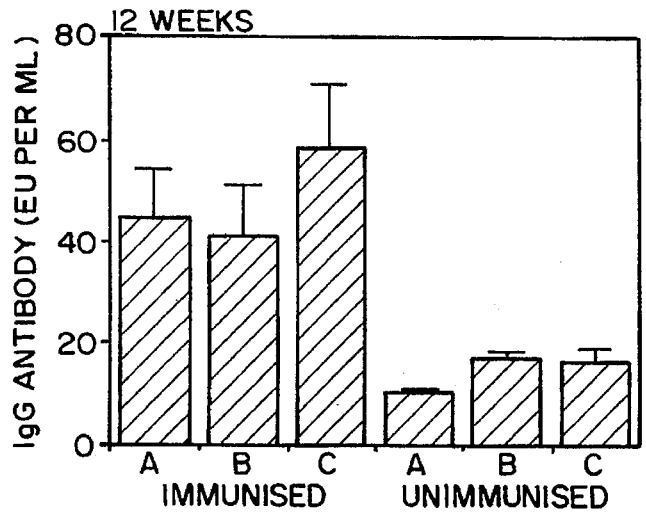

Homotypic cross protection induced by A/Qld/6/72 H3N2 to differing viruses within the H3N2 subtype is depicted in FIG. 10 while FIG. 11 correlates antibody titre and homotypic cross protection in this system.

Figure 9:
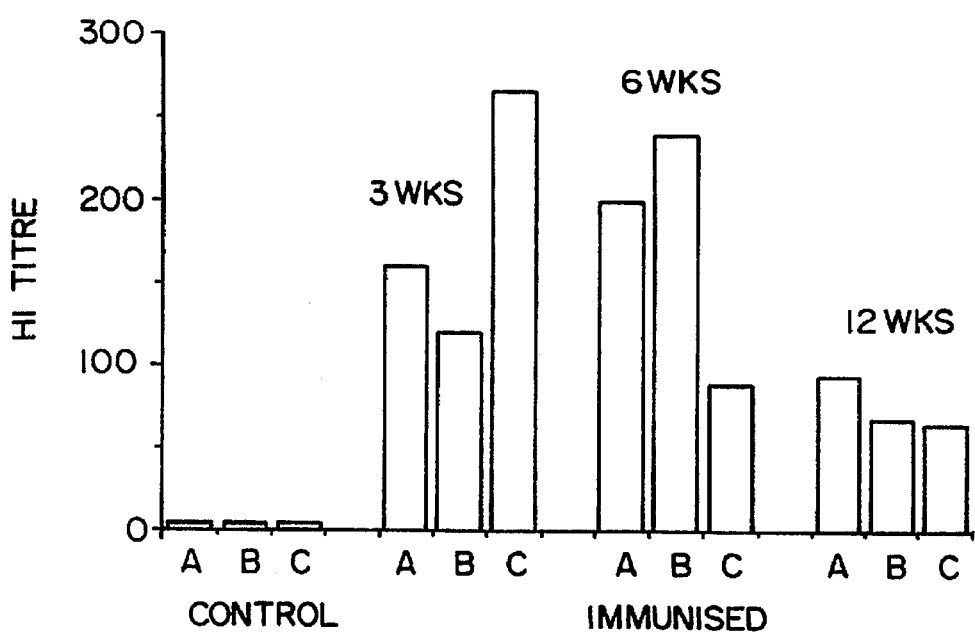
FIG. 9 is a bar graph depicting haemagglutination inhibition titre in lung homogenates of mice following oral immunisation with CRBC adsorbed with A/Qld/6/72 (H3N3) virus.

A remarkable level of cross protection (across the haemagglutinin barrier) was demonstrated using ELISA antibody assay. This cross protection could be directly demonstrated using in vivo challenge. This protection (antibody production and pulmonary clearance) could be demonstrated to remain relatively undiminished for at least three months: following a primary immunization. Antigen specificity was further examined using haemagglutination inhibition titres, and again, cross protection was demonstrated, indication an extraordinary production of haemagglutinin specific antibodies (FIG. 9), although by 12 weeks antibody titres were falling.

Figure 7:
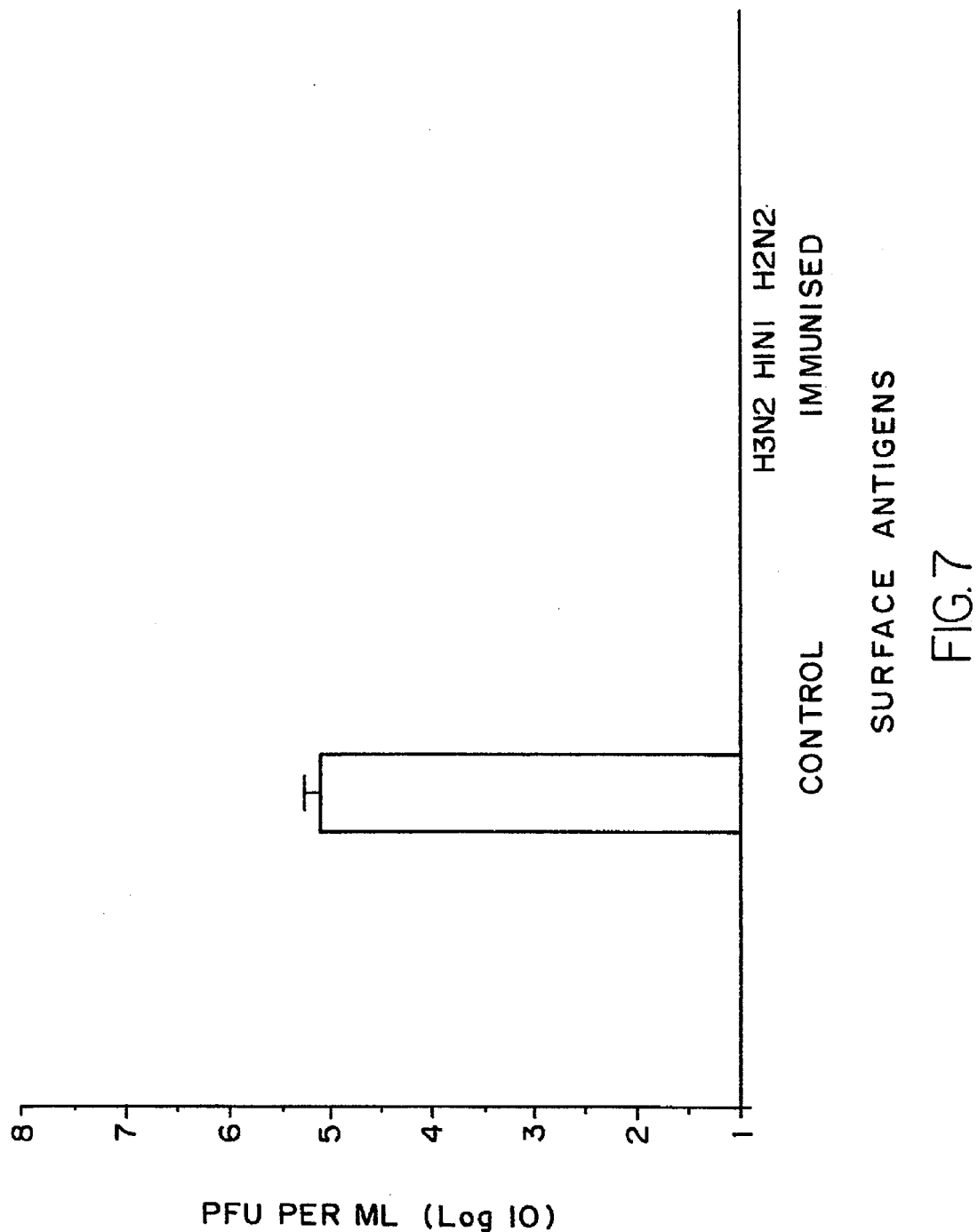
FIG. 7 is a bar graph of a comparative experiment depicting cross protection of mice to H2N2 and H1N1 viruses after oral vaccination with live H3N3 viruses (A/Qld/6/72)

Thus it would appear that immunization with this embodiment of the invention stimulates a broad immunity that crosses the "haemagglutinin barrier" of systemic immunisation using a very small Mount of virus. By way of example, FIG. 7 indicates that cross protection is not seen in orally administered influenza vaccine in the absence of the red blood cells (or derivatives).

Although the invention has been illustrated using a murine model employing gamma irradiated influenza virus in association with chicken red blood cell derivatives it will be appreciated that other systems including human fall within the spirit and scope of the invention.

What is claimed is:

1. An oral vaccine comprising an influenza antigen, wherein said influenza antigen is surface-associated with a red blood cell or a ghost preparation thereof, and wherein said vaccine elicits a mucosal immune response in mammals.

2. A vaccine according to claim 1 wherein the influenza antigen comprises influenza virus inactivated by gamma irradiation.

3. A vaccine according to claim 1 wherein the antigen is adsorbed to the surface of the red blood cell or ghost preparation thereof.

4. A vaccine according to claim 1 wherein the antigen is chemically coupled to the red blood cell or ghost preparation thereof.

5. A vaccine according to claim 1 wherein the antigen binds an indigenous surface receptor of the red blood cell or ghost preparation thereof.

6. A method for eliciting a mucosal immune response in a mammal, said method comprising orally administering to said mammal a vaccine as claimed in claim 1 in an amount effective to elicit said mucosal immune response.

7. The vaccine according to claim 1 wherein said influenza antigen is influenza type A.

8. The vaccine according to claim 1 wherein the red blood cell is a chicken red blood cell or ghost preparation thereof.

9. The vaccine according to claim 1 wherein the red blood cell is a duck red blood cell or ghost preparation thereof.

10. The vaccine according to claim 1 wherein the red blood cell is a cow red blood cell or ghost preparation thereof.

11. The vaccine according to claim 1 wherein the red blood cell is a sheep red blood cell or ghost preparation thereof.

12. The vaccine according to claim 1 wherein the red blood cell is a human red blood cell or ghost preparation thereof.

13. An oral vaccine comprising an influenza Type A antigen, wherein said influenza antigen is surface-associated with a red blood cell or a ghost preparation thereof, and wherein said vaccine elicits a mucosal immune response in mammals.

* * * * *